United States Patent [19]

Suzuki et al.

[11] Patent Number: 5,192,768
[45] Date of Patent: Mar. 9, 1993

[54] PYRAZOLOQUINOLINE DERIVATIVES

[75] Inventors: Fumio Suzuki; Yoshisuke Nakasato; Kenji Ohmori; Tadafumi Tamura; Hisashi Hosoe; Kazuhiro Kubo; Ikufumi Yoshitake, all of Shizuoka, Japan

[73] Assignee: Kyowa Hakko Kogyo Co., Ltd., Tokyo, Japan

[21] Appl. No.: 757,988

[22] Filed: Sep. 12, 1991

[30] Foreign Application Priority Data

Sep. 14, 1990 [JP] Japan .................. 2-245389

[51] Int. Cl.$^5$ .................. C07D 471/04; A61K 31/44
[52] U.S. Cl. .................. 514/293; 546/82
[58] Field of Search .................. 546/82; 514/303, 293

[56] References Cited

U.S. PATENT DOCUMENTS 4,524,146 6/1985 Yokoyama .................. 514/273
4,675,324 6/1987 Ueda et al. .................. 514/293
4,748,246 5/1988 Skotnicki et al. .................. 514/331

OTHER PUBLICATIONS

Kumar, et al., J. Chem. Soc. Perkin Trans I, (8), pp. 857-862 (1978).

*Primary Examiner*—Alan L. Rotman
*Attorney, Agent, or Firm*—Fitzpatrick, Cella, Harper & Scinto

[57] ABSTRACT

A pyrazoloquinoline derivative having the formula (I):

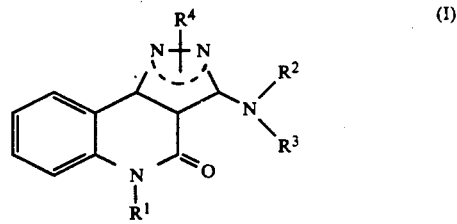

wherein $R^1$, $R^2$, and $R^3$ independently represent a hydrogen atom or a lower alkyl group; $R^4$ represents a hydrogen atom, a lower alkyl group, a halogen-substituted lower alkyl group, or a lower alkoxycarbonyl group; the dotted line means that the pyrazole ring has two conjugated double bonds; and $R^4$ is bonded to the nitrogen atom at the 1-position or 2-position, or pharmacologically acceptable salts thereof. These compounds exhibit excellent anti-inflammatory activity and hepatic insufficiency treating activity.

6 Claims, No Drawings

PYRAZOLOQUINOLINE DERIVATIVES

FIELD OF THE INVENTION

This invention relates to 3-aminopyrazolo[4,3-c]quinolin-4-one derivatives useful as anti-inflammatory agents and treating agents for hepatic insufficiency.

BACKGROUND OF THE INVENTION

Compounds having a 3-aminopyrazol[4,3-c]quinolin-2-one skeleton are unknown. 3-Amino-6,7,8,9-tetrahyiropyrazolo[4,3-c]quinolin-4-one derivatives represented by formula:

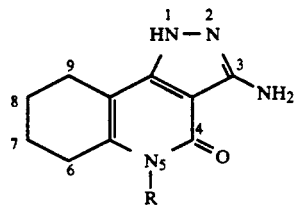

wherein R represents a hydrogen atom or a methyl group, which are deemed structurally relevant to the compounds of the present invention are described in *Journal of Chemical Society, Pirkin I*, p. 857 (1978), but their pharmacological activities are entirely unknown.

SUMMARY OF THE INVENTION

An object of the present invention is to provide a 3-aminopyrazolo[4,3-c]quinolin-4-one derivative having excellent anti-inflammatory activity or hepatic insufficiency treating activity.

The present invention relates to a pyrazoloquinoline derivative having the formula (I):

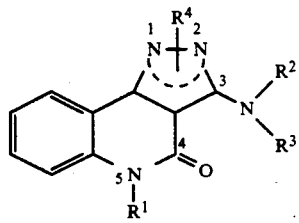 (I)

wherein $R^1$, $R^2$, and $R^3$ independently represent a hydrogen atom or a lower alkyl group; $R^4$ represents a hydrogen atom, a lower alkyl group, a halogen-substituted lower alkyl group or a lower alkoxycarbonyl group; the dotted line means that the pyrazole ring has two conjugated double bonds; and $R^4$ is bounded to the nitrogen atom at the 1-position or 2-position, or pharmacologically acceptable salts thereof. These compounds are hereinafter collectively referred to as the compounds of formula (I) or compound (I).

DETAILED DESCRIPTION OF THE INVENTION

In formula (I), the alkyl moiety in the lower alkyl, halogen-substituted lower alkyl and lower alkoxycarbonyl groups is a straight chain or branched alkyl group having from 1 to 6 carbon atoms, e.g., methyl, ethyl, propyl, isopropyl, butyl, isobutyl, sec-butyl, tert-butyl, pentyl, neopentyl, or hexyl groups.

The halogen-substituted lower alkyl group has from 1 to 3 halogen atoms which may be the same or different, e.g., fluorine, chlorine, bromine, or iodine atoms.

Salts of the compounds of formula (I) preferably include pharmacologically acceptable acid addition salts.

The pharmacologically acceptable acid addition salts of the compound of formula (I) include inorganic acid salts, e.g., hydrochloride, sulfate, or phosphate; and organic acid salts, e.g., acetate, maleate, fumarate, tartrate, and citrate.

Compounds of formula (I) wherein $R^4$ is a hydrogen atom generally exist as tautomers represented by formulae (I-1) and (I-2):

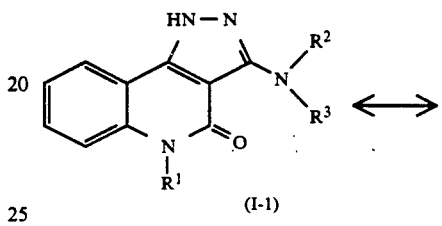

(I-1)

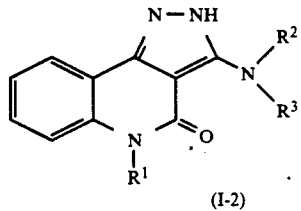

(I-2)

For the sake of convenience, these tautomers will hereinafter be inclusively represented by formula (I-1).

ORGANIC SYNTHESIS

The compounds of formula (I) can be prepared, for example, by Processes (a) to (e) illustrated below.

(a)

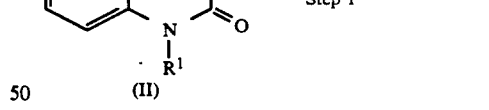

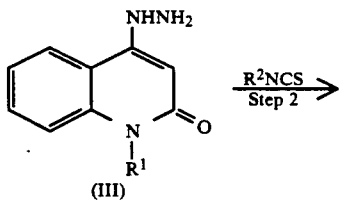

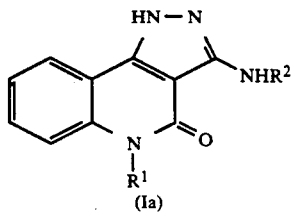

(Ia)

(Ia) → 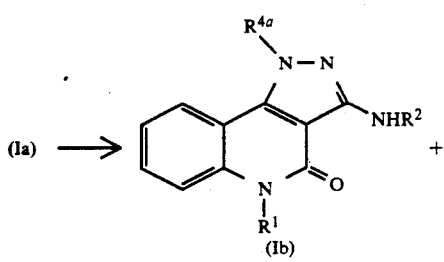

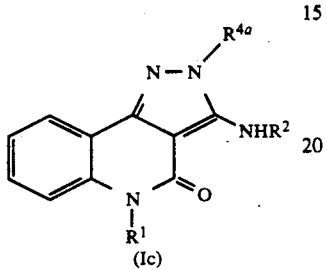

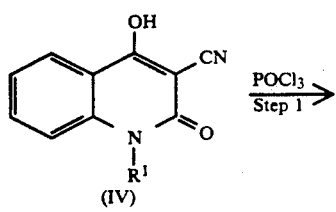

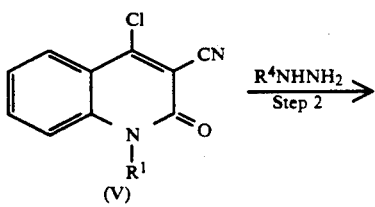

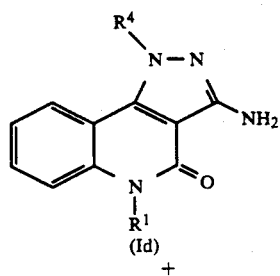

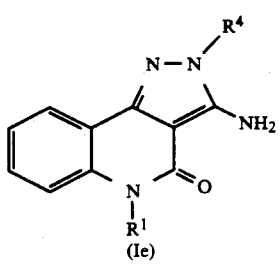

(Ib), (Id) → 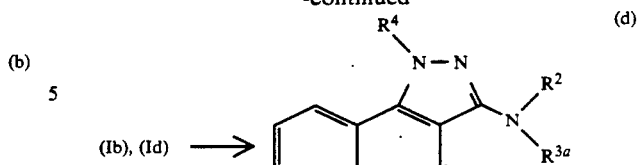

(Ic), (Ie) → 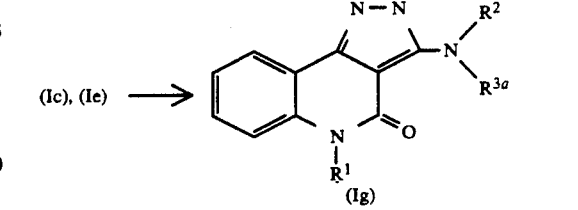

In the above formulae, the definition of $R^1$, $R^2$, $R^3$ and $R^4$ have the same significance as defined above; $R^{4a}$ represents lower alkyl, halogen-substituted lower alkyl or lower alkoxycarbonyl groups in the definition of $R^4$; and $R^{3a}$ represents a lower alkyl group in the definition of $R^3$.

In Step 1 of (a), 1 mol of compound (II) is reacted with 2 to 5 mols of hydrazine hydrate in an alcohol solvent, e.g., methanol, ethanol, or propanol, at room temperature to 100° C. for 0.5 to 3 hours. Thus compound (III) can be obtained.

Compound (II) wherein $R^1$ is a methyl group is known as disclosed in *Indian J. Chem. Section B*, 24B(1), 62 (1985). Compound (II) wherein $R^1$ is other than a methyl group can be synthesized according to the process disclosed therein.

In Step 2 of (a), 1 mol of compound (III) is reacted with 1 to 5 mols of an isothiocyanate ($R^2$-NCS) in a solvent, e.g., dimethylformamide, pyridine, dimethylacetamide, or dimethyl sulfoxide to obtain compound (Ia). The reaction is carried out at 50° to 130° C. for 3 to 40 hours preferably first at 50° to 70° C. for about 1 to 3 hours and then at an elevated temperature of 90° to 130° C. for 3 to 40 hours.

In process (b), compound (Ib) or (Ic) is obtained by displacing a hydrogen atom of the pyrazole ring of compound (Ia) with an alkyl group or an alkoxycarbonyl group.

Alkylating agents for introduction of an alkyl group include alkyl halides, e.g., methyl iodide, ethyl iodide, propyl iodide, isopropyl iodide, butyl iodide, or butyl bromide. Introduction of an alkoxycarbonyl group is preferably effected by using methyl chlorocarbonate, ethyl chlorocarbonate, etc. From 1 to 10 mols of the alkylating or alkoxycarbonylating agent is reacted with per mol of compound (Ia) in a solvent, e.g., dimethylformamide, dimethylacetamide, or dioxane at room temperature to 50° C. for 1 to 20 hours. To accelerate the reaction, the reaction may be carried out in the presence of a deacidifying agent, e.g., sodium hydride, potassium carbonate, sodium carbonate, triethylamine, or pyridine. Pyridine may also serve as a solvent.

The reaction of process (b) generally produces compound (Ib) as a main product. Separation of compound (Ib) from compound (Ic), unreacted components and other products can be performed by usual purification means such as silica gel column chromatography and the like.

Step 1 of (c) is carried out by treating compound (IV) with phosphorus oxychloride at room temperature to 140° C. for 1 to 5 hours to obtain compound (V).

Compound (IV) wherein $R^1$ is a methyl group is known as described in *J. Heterocycl. Chem.*, 16(8), 1605 (1979). Other compounds (IV) are synthesized according to the process disclosed therein.

In Step 2 of (c), 1 mol of compound (V) is reacted with 2 to 5 mols of a substituted hydrazine ($R^4NHNH_2$) in an alcohol solvent, e.g., methanol, ethanol, propanol, or 2-methoxyethanol. Thus, compound (Id) and (Ie) are obtained. The reaction is performed at room temperature to 100° C. for 1 to 5 hours. The reaction products, compound (Id) and compound (Ie), can be separated into each component by usual purification techniques, such as silica gel column chromatography.

In process (d), a mono- or disubstituted compound (If) can be obtained by reacting compound (Ib) or (Id) with an alkylating agent, preferably in the presence of a deacidifying agent. Alkylating agents to be used include alkyl halides of the above-mentioned (b). The alkylating agent is used in an amount of 1 to 10 mols per mol of compound (Ib) or (Id) in a solvent, e.g., pyridine, dimethylformamide or dimethylacetamide. The reaction is preferably carried out at room temperature to 100° C. for 1 to 10 hours. Suitable deacidifying agents are potassium carbonate, sodium carbonate, triethylamine, or pyridine.

In process (e), compound (Ig) can be obtained according to the same procedure as process (d) except that compound (Ic) or (Ie) are used instead of compound (Ib) or (Id).

All the intermediate products and desired products obtained in the above-described processes can be isolated and purified by purification techniques commonly employed in organic synthesis, such as filtration, extraction, washing, drying, concentration, recrystallization, or chromatographic methods. Alternatively, the intermediate product may be subsequently reacted as is without purification.

When compound (I) in the form of a salt is desired, a product obtained in the form of a salt is purified as such, or a product obtained in the free form is converted to its salt by dissolving or suspending it in an appropriate solvent and adding an acid thereto.

Some compounds (I) or their pharmacologically acceptable salts exist in the form of an addition product with water or various solvents. Such addition products are also included in the scope of the present invention.

Specific embodiments of various compounds according to formula (I) obtained by processes (a) to (e) are shown in Tables 1 and 2 below.

TABLE 1

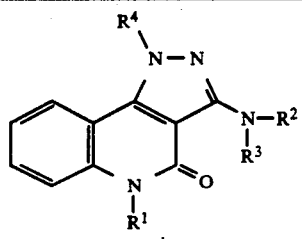

| Compound No. | $R^1$ | $R^2$ | $R^3$ | $R^4$ |
|---|---|---|---|---|
| 1 | $(CH_2)_2CH_3$ | $CH_3$ | H | H |
| 2 | $(CH_2)_2CH_3$ | $(CH_2)_3CH_3$ | H | H |
| 3 | $(CH_2)_2CH_3$ | $CH_3$ | H | $CO_2CH_3$ |
| 4 | $(CH_2)_2CH_3$ | $CH_3$ | H | $(CH_2)_3CH_3$ |
| 5 | $(CH_2)_2CH_3$ | $(CH_2)_3CH_3$ | H | $CO_2CH_3$ |

TABLE 2

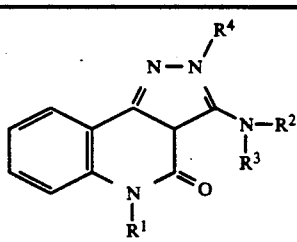

| Compound No. | $R^1$ | $R^2$ | $R^3$ | $R^4$ |
|---|---|---|---|---|
| 6 | $(CH_2)_2CH_3$ | H | H | $CO_2CH_3$ |
| 7 | $(CH_2)_2CH_3$ | H | H | $C(CH_3)_3$ |
| 8 | $(CH_2)_2CH_3$ | H | H | $CH_2CF_3$ |
| 9 | $(CH_2)_2CH_3$ | $CH_3$ | $CH_3$ | $CH_2CF_3$ |
| 10 | $(CH_2)_2CH_3$ | H | $CH_3$ | $CH_2CF_3$ |

PHARMACEUTICAL APPLICATIONS

Compound (I) or pharmacologically acceptable salts thereof can be used as it is or in various forms of preparations. Preparations can be obtained by uniformly mixing an effective amount of compound (I) or a pharmacologically acceptable salt thereof as an active ingredient with pharmacologically acceptable carriers. The preparations preferably have a unit dose form suitable for oral administration or injection.

For preparation of dose forms for oral administration, any useful and pharmacologically acceptable carriers can be used. For example, liquid preparations, e.g., suspensions or syrups, can be prepared by using water, saccharides, e.g., sucrose, sorbitol, or fructose; glycols, e.g., polyethylene glycol or propylene glycol; oils, e.g., sesame oil, olive oil, or soybean oil; antiseptics, e.g., p-hydroxybenzoic esters; or flavors, e.g., strawberry flavor or peppermint. Powders, pills, capsules, or tablets can be prepared by using vehicles, e.g., lactose, glucose, sucrose, or mannitol; disintegrators, e.g., starch or sodium alginate; lubricants, e.g., magnesium stearate or talc; binders, e.g., polyvinyl alcohol, hydroxypropyl cellulose, or gelatin; surface active agents, e.g., fatty acid esters; or plasticizers, e.g., glycerin. Tablets or capsules are the most useful unit dose forms for oral administration because of their ease of application. For preparation of tablets or capsules, solid carriers are employed.

Injectable solutions can be prepared by using carriers, such as distilled water, a salt solution, a glucose solution, or a mixture of a salt solution and a glucose solution.

For an aerosol for inhalation, the compound is dissolved in an appropriate pharmaceutically acceptable solvent, e.g., ethyl alcohol or a mixture of ethyl alcohol and a miscible solvent, and the solution is mixed with a pharmaceutically acceptable atomizing base.

The effective dose level and number of doses of compound (I) or a pharmacologically acceptable salt thereof vary depending on the administration route and the age, body weight and symptoms of a patient. A recommended daily dose is usually 1 to 50 mg/kg in 3 to 4 divided doses.

The present invention is now illustrated in greater detail with reference to the following Examples.

EXAMPLE 1

4-Hydrazino-1-propylquinolin-2(1H)-one (Compound a)

In 140 ml of ethanol was dissolved 6.02 g (27 mmol) of 4-chloro-1-propylquinolin-2(1H)-one, and 140 ml of hydrazine monohydrate was added thereto, followed by refluxing for 3 hours. The reaction mixture was concentrated to an about half of its original volume and then allowed to cool to obtain 5.53 g (94%) of the titled compound as a pale yellow crystal.

Melting point: 181°-186° C.

Elementary Analysis for $C_{12}H_{15}N_3O$: Calcd. (%): C 66.34; H 6.96; N 19.34. Found (%): C 66.50, H 7.18; N 19.62.

IR (KBr) $\nu_{max}$ (cm$^{-1}$): 1642, 748.

$^1$H-NMR (DMSO-$d_6$, 270 MHz) δ (ppm): 8.12 (1H, s), 7.94–7.91 (1H, m), 7.57–7.50 (1H, m), 7.43–7.40 (1H, m), 7.16–7.10 (1H, m), 5.86 (1H, s), 4.24 (2H, brs), 4.13–4.07 (2H, m), 1.62–1.53 (2H, m), 0.92 (3H, t, J=7Hz).

EXAMPLE 2

4-Chloro-1,2-dihydro-1-propyl-2-oxo-3-quinolinecarbonitrile (Compound b)

In 10 ml of phosphorus oxychloride was refluxed 1.0 g (4.1 mmol) of 1,2-dihydro-4-hydroxy-1-propyl-2-oxo-3-quinolinecarbonitrile for 1 hour. The reaction mixture was dried under reduced pressure, and the residue was partitioned between chloroform and water. The chloroform layer was dried under reduced pressure to obtain 0.44 g (41%) of the titled compound as a yellow crystal.

Melting point: 203°-205° C.

Elementary Analysis for $C_{13}H_{11}ClN_2O$: Calcd. (%): C 63.29; H 4.49; N 11.36. Found (%): C 63.23, H 4.33; N 11.45.

IR (KBr) $\nu_{max}$ (cm$^{-1}$): 2232, 1645, 762.

$^1$H-NMR (DMSO-$d_6$, 270 MHz) δ (ppm): 8.12–8.08 (1H, m), 7.94–7.87 (1H, m), 7.79–7.76 (1H, m), 7.53–7.47 (1H, m), 4.27–4.22 (2H, m), 1.71–1.63 (2H, m), 0.97 (3H, t, J=7Hz).

EXAMPLE 3

3-Methylamino-5-propyl-1H-pyrazolo[4,3-c]quinolin-4(5H)-one (Compound 1)

In 18 ml of N,N-dimethylformamide (DMF), 2.08 g (9.6 mmol) of Compound a prepared in Example 1 and 1.59 g (21.7 mmol) of methylthioisocyanate were stirred at 140° C. for 20 hours. Water was added to the reaction mixture, and the mixture was cooled and allowed to stand. The crystal thus formed was washed with ethyl acetate and then recrystallized from DMF-ethanol to obtain 0.76 g (30%) of the titled compound as a pale yellow crystal.

Melting 267°-270° C.

Elementary Analysis for $C_{14}H_{16}N_4O$: Calcd. (%): C 65.60; H 6.29; N 21.86. Found (%): C 65.39; H 6.58; N 21.71.

IR (KBr) $\nu_{max}$ (cm$^{-1}$): 1645, 748.

$^1$H-NMR (DMSO-$d_6$, 270 MHz) δ (ppm): 12.68 (1H, brs), 8.04–8.01 (1H, m), 7.57–7.51 (2H, m), 7.28–7.23 (1H, m), 5.53 (1H, brs), 4.20–4.14 (2H, m), 2.88 (3H, d, J=5Hz), 2.56–2.49 (2H, m), 0.94 (3H, t, J=7Hz).

MS, m/e: 256 (M+).

EXAMPLE 4

3-Butylamino-5-propyl-1H-pyrazolo[4,3-c]quinolin-4(5H)-one (Compound 2)

In 150 ml of DMF, 15.0 g (69 mmol) of Compound a and 18.9 g (157 mmol) of butylthioisocyanate were stirred at 140° C. for 40 hours. Water was added to the reaction mixture, followed by cooling. The precipitate thus formed was subjected to silica gel column chromatography using a 30:1 (by volume) mixed solvent of chloroform and methanol as an eluent. The main fraction was collected, dried under reduced pressure, and recrystallized from water-containing ethanol to obtain 2.0 g (10 %) of the titled compound as a pale yellow crystal.

Melting point: 169°-172° C.

IR (KBr) $\nu_{max}$ (cm$^{-1}$): 1660, 1581, 747.

$^1$H-NMR (DMSO-$d_6$, 270 MHz) δ (ppm): 12.6 (1H, brs), 8.03–8.00 (1H, m), 7.58–7.52 (2H, m), 7.29–7.23 (1H, m), 5.60 (1H, brs), 4.19–4.13 (2H, m), 3.30–3.25 (2H, m), 1.70–1.54 (4H, m), 1.44–1.30 (2H, m), 0.97–0.87 (6H, m).

MS, m/e: 298 (M+).

EXAMPLE 5

1-Methoxycarbonyl-3-methylamino-5-propyl-1H-pyrazolo[4,3-c]quinolin-4(5H)-one (Compound 3)

In 70 ml of DMF was suspended 1.69 g (6.6 mmol) of Compound 1, and 0.33 g (8.3 mmol) of 60% sodium hydride was added and dissolved therein. To the mixture was added 0.80 ml (10 mmol) of methyl chlorocarbonate, followed by stirring at room temperature for 1 hour. The reaction mixture was dried under reduced pressure, and the residue was partitioned between chloroform and water. The chloroform layer was dried under reduced pressure, passed through a silica gel column, and eluted with chloroform. The main fraction collected was dried under reduced pressure and recrystallized from water-containing ethanol to obtain 1.03 g (50%) of the titled compound as a colorless crystal.

Melting point: 160°-163° C.

Elementary Analysis for $C_{16}H_{18}N_4O_3$: Calcd. (%): C 61.13; H 5.77; N 17.82. Found (%): C 61.08, H 6.01; N 17.94.

IR (KBr) $\nu_{max}$ (cm$^{-1}$): 1749, 1660.

$^1$H-NMR (DMSO-$d_6$, 270 MHz) δ (ppm): 8.93–8.89 (1H, m), 7.69–7.67 (2H, m), 7.35–7.29 (1H, m), 6.26 (1H, brq, J=5Hz), 4.30–4.24 (2H, m), 4.02 (3H, s), 2.90 (3H, d, J=5Hz), 1.72–1.63 (2H, m), 0.96 (3H, t, J=7Hz).

MS, m/e: 314 (M+).

EXAMPLE 6

1-Butyl-3-methylamino-5-propyl-1H-pyrazolo[4,3-c]quinolin-4(5H)-one (Compound 4)

In 70 ml of DMF was suspended 1.00 g (3.9 mmol) of Compound 1, and 0.20 g (5.0 mmol) of 60% sodium hydride was added and dissolved therein. To the mixture was added 0.88 ml (7.7 mmol) of butyl iodide, followed by stirring at room temperature for 1 hour. The reaction mixture was dried under reduced pressure, and the residue was partitioned between chloroform and water. The chloroform layer was dried under reduced pressure, passed through a silica gel column, and eluted with chloroform. The main fraction collected was dried under reduced pressure and recrystallized from water-containing ethanol to obtain 0.55 g (45%) of the titled compound as a colorless crystal.

Melting point: 125°-127° C.
IR (KBr) $\nu_{max}$ (cm$^{-1}$): 1645, 750.
$^1$H-NMR (DMSO-d$_6$, 270 MHz) δ (ppm): 8.06-8.03 (1H, m), 7.60-7.55 (2H, m), 7.36-7.30 (1H, m), 4.45 (2H, t, J=7Hz), 4.22-4.17 (2H, m), 2.88 (3H, s), 1.83-1.59 (4H, m), 1.42-1.34 (2H, m), 0.95 (3H, t, J=7Hz), 0.92 (3H, t, J=7Hz).
MS, m/e: 312.

EXAMPLE 7

3-Butylamino-1-methoxycarbonyl-5-propyl-1H-pyrazolo[4,3-c]quinolin-4(5H)-one (Compound 5)

In 60 ml of dioxane was suspended 1.40 g (4.7 mmol) of Compound 2, and 1.0 ml (7.2 mmol) of triethylamine and 0.73 ml (9.4 mmol) of methyl chlorocarbonate were added thereto, followed by stirring at room temperature for 2 hours. The reaction mixture was dried under reduced pressure, and the residue was partitioned between chloroform and water. The chloroform layer was dried under reduced pressure, and the residue was passed through a silica gel column and eluted with a 3:1 (by volume) mixed solvent of hexane and ethyl acetate. The main fraction collected was recrystallized from hexane-ethyl acetate to obtain 0.67 g (40%) of the titled compound as a colorless crystal.

Melting point: 147°-149° C.
IR (KBr) $\nu_{max}$ (cm$^{-1}$): 1740, 1661, 762.
$^1$H-NMR (DMSO-d$_6$, 270 MHz) δ (ppm): 8.93-8.90 (1H, m), 7.70-7.67 (2H, m), 7.36-7.30 (1H, m), 6.14 (1H, brt, J=6Hz), 4.30-4.27 (2H, m), 4.02 (3H, s), 3.35-3.23 (2H, m), 1.72-1.57 (4H, m), 1.43-1.34 (2H, m), 0.97 (3H, s, J=7Hz), 0.93 (3H, s, J=7Hz).
MS, m/e: 356 (M+).

EXAMPLE 8

3-Amino-2-methoxycarbonyl-5-propyl-2H-pyrazolo[4,3-c]quinolin-4(5H)-one (Compound 6)

In 60 ml of methanol were refluxed 2.00 g (8.1 mmol) of Compound b prepared in Example 2 and 1.10 g (12.2 mmol) of methoxycarbonylhydrazine for 6 hours. The reaction mixture was cooled to obtain 1.32 g (54%) of the titled compound as a colorless crystal.

Melting point: 180°-184° C.
Elementary Analysis for C$_{15}$H$_{16}$N$_4$O$_3$: Calcd. (%): C 59.99; H 5.37; N 18.66. Found (%): C 60.21, H 5.42; N 18.36.
IR (KBr) $\nu_{max}$ (cm$^{-1}$): 1746, 1651.
$^1$H-NMR (DMSO-d$_6$, 270 MHz) δ (ppm): 8.03-8.00 (1H, m), 7.61-7.54 (1H, m), 7.47-7.44 (1H, m), 7.36 (2H, brs), 7.26-7.21 (1H, m), 4.14-4.08 (2H, m), 4.02 (3H, s), 1.67-1.62 (2H, m), 0.95 (3H, t, J=7Hz).
MS, m/e: 300 (M+).

EXAMPLE 9

3-Amino-2-t-butyl-5-propyl-2H-pyrazolo[4,3-c]quinolin-4(5H)-one (Compound 7)

In a mixture of 60 ml of ethanol and 5 ml of triethylamine, 2.00 g (8.1 mmol) of Compound b and 2.00 g (16 mmol) of t-butylhydrazine hydrochloride were refluxed for 4 hours. The reaction mixture was dried under reduced pressure, and the residue was partitioned between chloroform and water. The chloroform layer was dried under reduced pressure, and the residue was passed through a silica gel column and eluted with a 3:1 (by volume) mixed solvent of hexane and ethyl acetate. The main fraction collected was dried under reduced pressure to obtain 2.11 g (87%) of Compound 7 as a colorless crystal. The product was treated with ethyl acetate saturated with hydrogen chloride to obtain a hydrochloride of Compound 7.

Melting point: 175°-177° C.
Elementary Analysis for C$_{17}$H$_{22}$N$_4$O.HCl: Calcd. (%): C 60.98; H 6.92; N 16.73. Found (%): C 61.10, H 7.22; N 16.80.
IR (KBr) $\nu_{max}$ (cm$^{-1}$): 1662, 760.
$^1$H-NMR (DMSO-d$_6$, 270 MHz) δ (ppm): 8.00-7.97 (1H, m), 751-7.41 (2H, m), 7.22-7.16 (1H, m), 6.17 (2H, brs), 4.15-4.10 (2H, m), 1.71-1.58 (2H, m), 1.65 (9H, s), 0.94 (3H, t, J=7Hz).
MS, m/e: 298 (M+).

EXAMPLE 10

3-Amino-5-propyl-2-(2,2,2-trifluoroethyl)-2H-pyrazolo[4,3-c]quinolin-4(5H)-one (Compound 8)

In 60 ml of ethanol, 2.00 g (8.1 mmol) of Compound b and 1.94 ml (16 mmol) of 2,2,2-trifluoroethylhydrazine were refluxed for 6 hours. The reaction mixture was cooled to obtain 1.73 g (66%) of a colorless crystal. The product was treated with ethyl acetate saturated with hydrogen chloride to obtain a hydrochloride.

Melting point: 235°-237° C.
Elementary Analysis for C$_{15}$H$_{15}$F$_3$N$_4$O.HCl: Calcd. (%): C 49.94; H 4.47; N 15.53. Found (%): C 50.23, H 4.40; N 15.18.
IR (KBr) $\nu_{max}$ (cm$^{-1}$): 1640, 766.
$^1$H-NMR (DMSO-d$_6$, 270 MHz) δ (ppm): 7.97-7.94 (1H, m), 7.54-7.42 (2H, m), 7.23-7.17 (1H, m), 6.81 (2H, brs), 5.10 (2H, q, J=9Hz), 4.16-4.10 (2H, m), 1.70-1.56 (2H, m), 0.95 (3H, t, J=7Hz).
MS, m/e: 324 (M+).

EXAMPLE 11

3-Dimethylamino-5-propyl-2-(2,2,2-trifluoroethyl)-2H-pyrazolo[4,3-c]quinolin-4(5H)-one (Compound 9) and 3-Methylamino-5-propyl-2-(2,2,2-trifluoroethyl)-2H-pyrazolo[4,3-c]quinolin-4(5H)-one (Compound 10)

In 150 ml of DMF was dissolved 2.26 g (7.0 mmol) of a hydrochloride of Compound 8 obtained in Example 10, and 0.42 g (11 mmol) of 60% sodium hydride was added to the solution. After stirring at room temperature for 30 minutes, 0.87 ml (14 mmol) of methyl iodide was added thereto, followed by stirring for 1 hour. The reaction mixture was dried under reduced pressure, and the residue was partitioned between chloroform and water. The chloroform layer was dried under reduced pressure, and the residue was passed through a silica gel column and eluted with chloroform. The first main fraction collected was dried under reduced pressure to obtain 0.65 g (25%) of Compound 9 as a colorless crystal.

Melting point: 142.5°–145.5° C.

Elementary Analysis for $C_{17}H_{19}F_3N_4O$: Calcd. (%): C 57.95; H 5.43; N 15.90. Found (%): C 57.97, H 5.10; N 15.90.

IR (KBr) $\nu_{max}$ (cm$^{-1}$): 1661, 1174, 747.

$^1$H-NMR (DMSO-d$_6$, 270 MHz) δ (ppm): 8.14–8.11 (1H, m), 7.62–7.52 (2H, m), 7.31–7.25 (1H, m), 5.21 (2H, q, J=9Hz), 4.24–4.18 (2H, m), 2.86 (6H, s), 1.71–1.62 (2H, m), 0.98 (3H, t, J=7Hz).

MS, m/e: 352 (M+), 337, 323.

The second main fraction was collected and dried under reduced pressure to obtain 1.10 g (47%) of a colorless crystal (Compound 10), which was then treated with ethyl acetate saturated with hydrogen chloride to obtain a hydrochloride of Compound 10.

Melting point: 168.0°–168.5° C.

IR (KBr) $\nu_{max}$ (cm$^{-1}$): 3324, 1616, 1159, 752.

$^1$H-NMR (DMSO-d$_6$, 270 MHz) δ (ppm): 8.01–7.97 (1H, m), 7.53–7.40 (2H, m), 7.22–7.16 (1H, m), 5.13 (2H, q, J=9Hz), 4.15–4.09 (2H, m), 3.90 (brs, 1H), 3.27 (3H, s), 1.66–1.58 (2H, m), 0.96 (3H, t, J=7Hz).

MS, m/e: 338 (M+), 309, 296.

EXAMPLE 12

Pharmaceutical Composition

Tablets were prepared from the following components in a usual manner.

| Compound 1 | 50 mg |
|---|---|
| Lactose | 113 mg |
| Potato starch | 30 mg |
| Hydroxypropyl cellulose | 6 mg |
| Magnesium stearate | 0.6 mg |

EXAMPLE 13

Pharmaceutical Composition

A powder was prepared from the following components in a usual manner.

| Compound 1 | 50 mg |
|---|---|
| Lactose | 750 mg |

EXAMPLE 14

Pharmaceutical Composition

A syrup was prepared from the following components in a usual manner.

| Compound 1 | 50 mg |
|---|---|
| Purified sugar | 75 mg |
| Ethyl p-hydroxybenzoate | 100 mg |
| Propyl p-hydroxybenzoate | 25 mg |
| Strawberry flavor | 0.25 cc |
| Water to make | 100 cc |

EXAMPLE 15

Pharmaceutical Composition

Capsules were prepared from the following composition in a usual manner.

| Compound | 150 mg |
|---|---|
| Microcrystalline cellulose | 69.5 mg |
| Magnesium stearate | 0.5 mg |

The above components were mixed and filled in gelatin capsules.

EXAMPLE 16

Pharmaceutical Composition

An injectable solution was prepared from the following components in a usual manner.

| Compound 1 | 10 mg |
|---|---|
| Buffer | adequate amount |
| Water to make | 1.0 ml |

Typical pharmacological activities of compound (I) are demonstrated by Examples 17 and 18.

EXAMPLE 17

Effect on Type III Allergic Pleurisy in Rats

1. Preparation of IgG fraction of rabbit anti-egg white (anti-OA)

IgG was purified from rabbit anti-OA serum prepared in advance by the method of Koda et al. [Folia Pharmacol., Japon, 66, 237 (1970)] in the following manner.

A saturated solution of ammonium sulfate (half volume of the serum) was added to the anti-OA serum, and the mixture was left for one hour at 4° C. The precipitate was taken by centrifugation (3,000 rpm, 30 min, 4° C.) and dissolved in phosphate buffered saline of Dulbecco. Then, ammonium sulfate fractionation was carried out three times in the same manner as above, whereby a purified IgG fraction was obtained.

2. Type III allergic reaction-induced pleurisy

Male Wister rats weighing 225–250 g were pre-bred for several days and fasted overnight prior to experiment. The test compound (100 mg/kg) was orally administered to the animals, and after 30 minutes, IgG of rabbit anti-OA (0.2 ml, 5 mg protein/ml) was injected into the pleural cavity of the animals under anesthesia with ether. Thirty minutes after the injection of IgG, OA (albumin egg grade III; Sigma Chemical Co.) was intravenously injected into the animals as an inducer of pleurisy. After two hours, Evans Blue (25 mg/kg) was intravenously injected, and four and half hours after the injection of pleurisy, the animals were killed by bleeding. Then, an exudate in the pleural cavity was obtained, and the volume of the exudate was measured. The pleural cavity was rinsed with 5 ml of physiological saline and the rinsings were added to the exudate. The number of infiltrated cells in the mixture was counted and th volume of the dye in the mixture was determined by the absorption at 625 nm [Agents and Actions, 25, 326 (1988)]. The suppression rates for the volume of the exudate, the number of infiltrated cells and the volume of the dye in the pleural cavity were calculated by the following equation.

$$\text{Suppression rate (\%)} = 100 - \frac{S.V - N.V}{P.V - N.V} \times 100$$

S.V: the value obtained with the group administered with the test compound and in which pleurisy is induced N.V: the value obtained with the group in which pleurisy is not induced P.V: the value obtained with the group administered with no test compound and in which pleurisy is induced

TABLE 3

INHIBITION OF ALLERGIC PLEURISY IN RATS

| Compound | Suppression rate (%) | | |
|---|---|---|---|
| | Volume of exudate | Volume of dye in the exudate | Number of infiltrated cells in the exudate |
| 3 | 8.5 | 41.2 | 48.2 |
| 4 | 26.4 | 45.6 | 24.1 |
| *8Sa | 52.9 | 52.3 | 36.2 |

*Sa means an hydrochloride of compound 8.

EXAMPLE 18

Inhibition of Hepatic Insufficiency Model

Effect of test compounds on hepatic insufficiency was measured by the following method [Acta. Hepatol. Japon, 26, 1438 (1985)]. Blood cells of *Propionibacterium acnes* (1 mg/mouse) was applied to 8-week-old male BALB/c mice (30 mice per group) by intravenous injection at the tail. After 7 days, 1 μg/mouse of lipopolysaccharide from *Salmonella enteritidis* was intravenously injected to induce acute hepatic insufficiency. At the same time, 100 mg/kg of compound (I) suspended in 0.3% carboxymethyl cellulose (CMC) was orally administered to mice (only 0.3% CMC was given to the control group). Mortality of animals were measured at 7 and 24 hours following the injection of lipopolysaccharide. The suppression effect of mortality of mice due to hepatic insufficiency were shown in Table 4. In Table 4, the value are calculated based on the decrease in mortality from control (untreated mice).

TABLE 4

INHIBITION OF MORTALITY OF MICE DUE TO HEPATIC INSUFFICIENCY

| Compound No. | Mortality | |
|---|---|---|
| | At 7 Hrs. | At 24 Hrs. |
| 1 | 39.2 | 17.9 |
| 3 | 42.0 | 13.9 |

TABLE 4-continued

INHIBITION OF MORTALITY OF MICE DUE TO HEPATIC INSUFFICIENCY

| Compound No. | Mortality | |
|---|---|---|
| | At 7 Hrs. | At 24 Hrs. |
| Control | 86.7 | 96.7 |

According to the present invention, there are provided 3-aminopyrazolo[4,3-c]quinolin-4-one derivatives exhibiting excellent anti-inflammatory activity and hepatic insufficiency treating activity.

While the invention has been described in detail and with reference to specific examples thereof, it will be apparent to one skilled in the art that various changes and modifications can be made therein without departing from the spirit and scope thereof.

What is claimed is:

1. A 3-aminopyrazolo [4,3-c]quinolin-4-one compound having the following formula (I):

(I)

wherein $R^1$, $R^2$, and $R^3$ independently represent a hydrogen atom or a lower alkyl group; $R^4$ represents a hydrogen atom, a lower alkyl group, a halogen-substituted lower alkyl group or a lower alkoxycarbonyl group; the dotted line means that the pyrazole ring has two conjugated double bonds; and $R^4$ is bounded to the nitrogen atom at the 1-position or 2-position, or pharmacologically acceptable salt thereof.

2. A 3-amino-pyrazolo[4,3-c]quinolin-4-one compound according to claim 1, wherein $R^4$ is bounded to the nitrogen atom at the 1 position; $R^1$ represents a lower alkyl group; and $R^2$ represents a lower alkyl group.

3. A 3-amino-pyrazolo[4,3-c]quinolin-4-one compound according to claim 2, wherein $R^1$ represents propyl.

4. A 3-amino-pyrazolo[4,3-c]quinolin-4-one compound according to claim 1, wherein $R^4$ is bounded to the nirogen atom at the 2 position; and $R^1$ represents a lower alkyl group.

5. A 3-amino-pyrazolo[4,3-c]quinolin-4-one compound according to claim 4, wherein $R^1$ represents propyl.

6. A pharmaceutical composition consisting essentially of an effective amount of a 3-amino-pyrazolo[4,3-c]quinolin-4-one compound according to the formula (I) of claim 1 in admixture with a pharmacologically acceptable carrier.

* * * * *

UNITED STATES PATENT AND TRADEMARK OFFICE
CERTIFICATE OF CORRECTION

PATENT NO. : 5,192,768                     Page 1 of 2
DATED     : March 9, 1993
INVENTOR(S) : FUMIO SUZUKI, ET AL.

It is certified that error appears in the above-identified patent and that said Letters Patent is hereby corrected as shown below:

COLUMN 1

Line 13, "rahyiropyrazolo" should read --rahydropyrazolo--.
Line 54, "bounded" should read --bonded--.

COLUMN 8

Line 5, "Melting" should read --Melting point:--.

COLUMN 9

Line 4, "clquinolin-" should read --c]quinolin- --.

COLUMN 10

Line 28, "751-7.41" should read --7.51-7.41--.

COLUMN 12

Line 8, "Compound" should read --Compound 1--.
Line 63, "th" should read --the--.

COLUMN 13

Line 50, "value" should read --values--.

COLUMN 14

Line 37, "bounded" should read --bonded--.
Line 38, "phar-" should read --a phar- --.
Line 41, "bounded" should read --bonded--.
Line 48, "bounded" should read --bonded--.

UNITED STATES PATENT AND TRADEMARK OFFICE
CERTIFICATE OF CORRECTION

PATENT NO. : 5,192,768

DATED : March 9, 1993

INVENTOR(S) : FUMIO SUZUKI, ET AL.

It is certified that error appears in the above-identified patent and that said Letters Patent is hereby corrected as shown below:

<u>COLUMN 14</u>

Line 49, "nirogen" should read --nitrogen--.

Signed and Sealed this

Eighteenth Day of January, 1994

*Attest:*

BRUCE LEHMAN

*Attesting Officer*   Commissioner of Patents and Trademarks